(12) United States Patent
Miller et al.

(10) Patent No.: US 9,786,402 B2
(45) Date of Patent: Oct. 10, 2017

(54) LIGHT SHIELDING APPARATUS

(71) Applicant: HONEYWELL FEDERAL MANUFACTURING & TECHNOLOGIES, LLC, Kansas City, MO (US)

(72) Inventors: Richard Dean Miller, Kansas City, MO (US); Robert Anthony Thom, Kansas City, MO (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 0 days.

(21) Appl. No.: 14/957,388

(22) Filed: Dec. 2, 2015

(65) Prior Publication Data

US 2017/0162289 A1   Jun. 8, 2017

(51) Int. Cl.
   *G02B 23/16*   (2006.01)
   *G21K 1/10*   (2006.01)
   *G21F 3/00*   (2006.01)

(52) U.S. Cl.
   CPC   *G21K 1/10* (2013.01); *G21F 3/00* (2013.01)

(58) Field of Classification Search
   CPC .................................................... H04N 5/225
   USPC ..................................................... 250/519.1
   See application file for complete search history.

(56) References Cited

U.S. PATENT DOCUMENTS

| | | | | |
|---|---|---|---|---|
| 4,576,459 A | * | 3/1986 | Miura | G03B 11/046 359/600 |
| 5,260,573 A | * | 11/1993 | Tsuchino | G01T 1/2014 250/584 |
| 7,083,291 B1 | * | 8/2006 | Yong | H04N 5/2251 348/834 |
| 7,529,479 B2 | * | 5/2009 | Watanabe | G03B 13/02 348/333.09 |
| 8,981,309 B2 | * | 3/2015 | Noguchi | G01T 1/20 250/370.01 |

* cited by examiner

*Primary Examiner* — Phillip A Johnston
(74) *Attorney, Agent, or Firm* — Hovey Williams LLP (57) ABSTRACT

A light shielding apparatus for blocking light from reaching an electronic device, the light shielding apparatus including left and right support assemblies, a cross member, and an opaque shroud. The support assemblies each include primary support structure, a mounting element for removably connecting the apparatus to the electronic device, and a support member depending from the primary support structure for retaining the apparatus in an upright orientation. The cross member couples the left and right support assemblies together and spaces them apart according to the size and shape of the electronic device. The shroud may be removably and adjustably connectable to the left and right support assemblies and configured to take a cylindrical dome shape so as to form a central space covered from above. The opaque shroud prevents light from entering the central space and contacting sensitive elements of the electronic device.

20 Claims, 6 Drawing Sheets

LIGHT SHIELDING APPARATUS

GOVERNMENT INTERESTS

This invention was developed with support from the U.S. government under a contract with the United States Department of Energy, Contract No. DE-NA0000622. Accordingly, the U.S. Government has certain rights in this invention.

BACKGROUND

The present invention relates to light shields for protecting electronic devices from exposure to light. Many electronic devices such as X-ray scanners, cameras, video equipment, motion detectors, and other electronic equipment have sensitive operational components that can be damaged or rendered ineffective when exposed to too much light. For example, overexposure of a phosphor panel of an X-ray scanner degrades the X-ray image and may erase the X-ray image altogether. Such overexposure may also damage the phosphor panel and other internal components. Electronic devices used outdoors and in well-lit areas are especially susceptible to overexposure risks and are therefore often fitted with light shields to block light from reaching their sensitive components. Unfortunately, conventional light shields often do not conform to contours of the electronic devices, thus allowing some light to pass between the light shields and the electronic devices. Light shields that do form a close fit are typically made specifically for one model of electronic device and cannot be adjusted or used with any other device.

SUMMARY

The present invention solves the above-described problems and provides a distinct advance in the art of light shields for electronic devices. More particularly, the present invention provides an adjustable light shield apparatus for blocking light from reaching sensitive components of an X-ray device, camera, video equipment, motion sensor, or other electronic device. The light shield can be adjusted to conform to electronic devices of different sizes and shapes.

An embodiment of the light shielding apparatus broadly includes left and right support assemblies, a cross member, and an opaque shroud.

The left and right support assemblies support the opaque shroud and provide rigidity to the light shielding apparatus. The left and right support assemblies each include primary support structure, a mounting component positioned on a proximal end of the primary support structure, and a lower support member depending from the primary support structure.

The primary support structure directly supports the opaque shroud and may include a sloped shroud engagement surface, support member fastener holes, cross member fastener holes, and shroud fastener holes. The sloped shroud engagement surface extends downwardly and outwardly from the primary support structure such that the sloped shroud engagement surfaces on both of the primary support structures cooperatively urge the opaque shroud into a cylindrical dome shape when the light shielding apparatus is assembled. The support member fastener holes receive support member fasteners for removably connecting the lower support member to the primary support structure. The support member fasteners may be spring plungers, thumb screws, bolts, or any other suitable fastener. The cross member fastener holes receive cross member fasteners for removably connecting the cross member to the primary support structure. The shroud fastener holes receive shroud fasteners for removably connecting the opaque shroud to the primary support structure. The shroud fastener holes may be positioned on an underside of the primary support structure below the sloped shroud engagement surface. The shroud fasteners may be thumb screws, bolts, pins, or any other suitable fastener. The primary support structure may be formed of rectangular tubing, molded plastic, or any other suitable material and may vary in size depending on the type and size range of electronic devices for which the light shielding apparatus may be used.

The mounting element is provided for removably connecting the light shielding apparatus to the front of the electronic device and broadly includes left and right hooks and a lower tab. The left and right hooks extend outwardly and downwardly from a proximal end of the primary support structure for engaging mounting slots on the electronic device. The lower tab extends outwardly below the left and right hooks for engaging a protrusion near the slots so as to prevent the hooks from being inadvertently dislodged from the slots.

The lower support member retains the light shielding apparatus in an upright orientation when the light shielding apparatus is connected to the electronic device and includes a downwardly extending section and a horizontally extending section. The downwardly extending section provides vertical spacing between the horizontally extending section and the primary support structure and may be angled towards the proximal end of the primary support structure. The horizontally extending section continues horizontally from the lower end of the downwardly extending section towards the proximal end of the primary support structure. The end of the horizontally extending section may include a flat, angled, or contoured rubber pad or rubber stop for contacting the electronic device. The lower support member may be removably or shiftably connected to the primary support structure via the support member fasteners for compact storage.

The cross member retains the left and right support assemblies in a coupled relationship with each other and may be connected to distal ends of the primary support structures or the vertically extending section of the lower support member via fasteners inserted into the cross member fastener holes. The cross member may be connected in one of a number of positions for spacing the primary support structures from each other according to the size and shape of the electronic device.

The opaque shroud blocks light from reaching the electronic device and may include a cover, left and right upturned portions, and left and right outwardly extending strips. The cover may be extended between the primary support structures of the left and right support assemblies and may take the shape of a cylindrical dome or similar shape when deployed so as to form a central space covered from above. The cover may have a predetermined radius or may be adjustable so as to conform to the shape of a front cap of the electronic device. The upturned portions extend from left and right edges of the cover on outer sides of the cover. The upturned portions may be connected to the cover via staples or other fasteners so as to form a reinforced region. The outwardly extending strips turn outward from the upturned portions so as to form flanges extending substantially the length of the cover. The outwardly extending strips may include fastener holes for receiving the shroud fasteners. The fastener holes may be elongated or open-ended slots for allowing the opaque shroud to be adjusted relative to the support assemblies. The opaque shroud may be formed of canvas, rubber, or any other substantially flexible material or molded plastic, sheet metal, or any other substantially rigid material.

The light shielding apparatus may be assembled by connecting the support members, cross member, and opaque shroud to the primary support structures of the left and right support assemblies. The opaque shroud may initially need to be manually urged into the cylindrical shape, while the inwardly sloping surfaces of the primary support structures help the opaque shroud retain the cylindrical dome shape.

The support assemblies may then be connected to the electronic device by pivoting the light shielding apparatus upwards so that the lower tabs of the mounting elements clear the mounting bosses of the electronic device. The left and right hooks of the mounting elements may then be inserted or lowered into the slots of the electronic device. The light shielding apparatus may then be pivoted downwards, once the lower tabs clear the mounting bosses, until the lower support members contact the lower portion of the electronic device. The opaque shield may be adjusted once the light shielding apparatus is mounted on the electronic device such that the cover overlaps or contacts the cap of the electronic device.

The light shielding apparatus may be removed from the electronic device by pivoting the light shielding apparatus upwards until the lower tabs of the mounting elements clear the mounting bosses of the electronic device. The light shielding apparatus may then be shifted upwards until the left and right hooks of the mounting elements are free from the slots of the electronic device. The lower support members, cross member, and opaque shroud may then be disconnected from the primary support structures and the opaque shroud may be folded or rolled up for compact storage.

The above described light shielding apparatus provides many advantages over the prior art. For example, the light shielding apparatus may be easily connected to the electronic device without removing the electronic device from its mount and may be used with many different sizes and types of electronic devices. The opaque shroud may be flexed or adjusted to ensure that light is prevented from reaching the electronic device between the front of the electronic device and the opaque shroud regardless of the shape of the front of the electronic device. In addition, the light shielding apparatus is lightweight and can be disassembled for compact storage.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to the drawing figures, a light shielding apparatus 10 constructed in accordance with a preferred embodiment of the invention is illustrated. The light shielding apparatus 10 blocks light from reaching an electronic device such as an X-ray scanner 100, camera, video equipment, motion detector, or other electronic device and broadly comprises left and right support assemblies 12, 14, a cross member 16, and an opaque shroud 18.

The left and right support assemblies 12, 14 support the opaque shroud 18 and provide rigidity to the light shielding apparatus 10. The left and right support assemblies 12, 14 each broadly include primary support structure 20, a mounting component 22 positioned on a proximal end of the primary support structure 20, and a lower support member 24 extending downwardly from the primary support structure 20.

Figure 6:
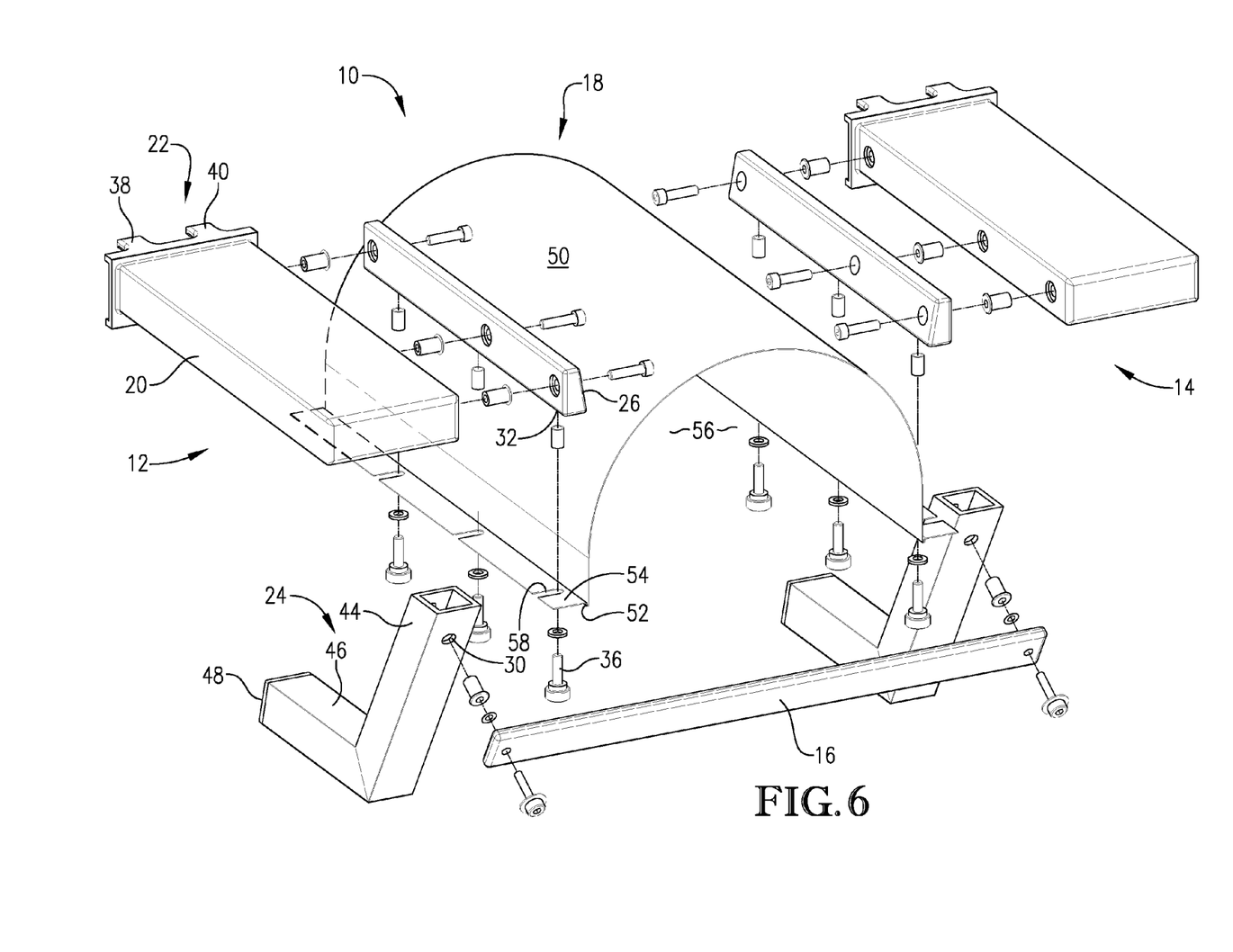
FIG. 6 is an exploded assembly view of the light shielding apparatus of FIG. 1.

The primary support structure 20 directly supports the opaque shroud 18 and may include a sloped shroud engagement surface 26, one or more support member fastener holes 28, one or more cross member fastener holes 30, and one or more shroud fastener holes 32. The sloped shroud engagement surface 26 extends downwardly and outwardly from the primary support structure 20 towards the opposite support assembly and engages lower portions of the opaque shroud 18 such that the sloped shroud engagement surfaces 26 on both of the primary support structures 20 cooperatively urge the opaque shroud 18 into a cylindrical dome as described below. The one or more support member fastener holes 28 receive support member fasteners 34 for removably connecting the lower support member 24 to the primary support structure 20 and may be positioned on a side or bottom of the primary support structure 20. The support member fasteners 34 may be spring plungers, thumb screws, bolts, or any other suitable fastener. The cross member fastener holes 30 receive cross member fasteners for removably connecting the cross member 16 to the primary support structure 20 and may be positioned on the distal end of the primary support structure 20. Alternatively, the cross member fastener holes 30 may be positioned on the downwardly extending sections 44 of the lower support members 24, as shown in FIG. 6. The shroud fastener holes 32 receive shroud fasteners 36 for removably connecting the opaque shroud 18 to the primary support structure 20 and may be positioned on an underside of the primary support structure 20 below the sloped shroud engagement surface 26. The shroud fasteners 36 may be thumb screws, bolts, pins, or any other suitable fastener. The primary support structure 20 may be approximately five inches to approximately fifteen inches long, approximately one inch to approximately four inches wide, and approximately one half of an inch to two inches tall, or any other suitable length, width, and height. The primary support structure 20 may be formed of rectangular tubing, molded plastic, or any other suitable shape and material. It will be understood that the primary support structure 20 may be larger or smaller depending on the type and size of the electronic device 100 for which the light shielding apparatus 10 may be used.

Figure 3:
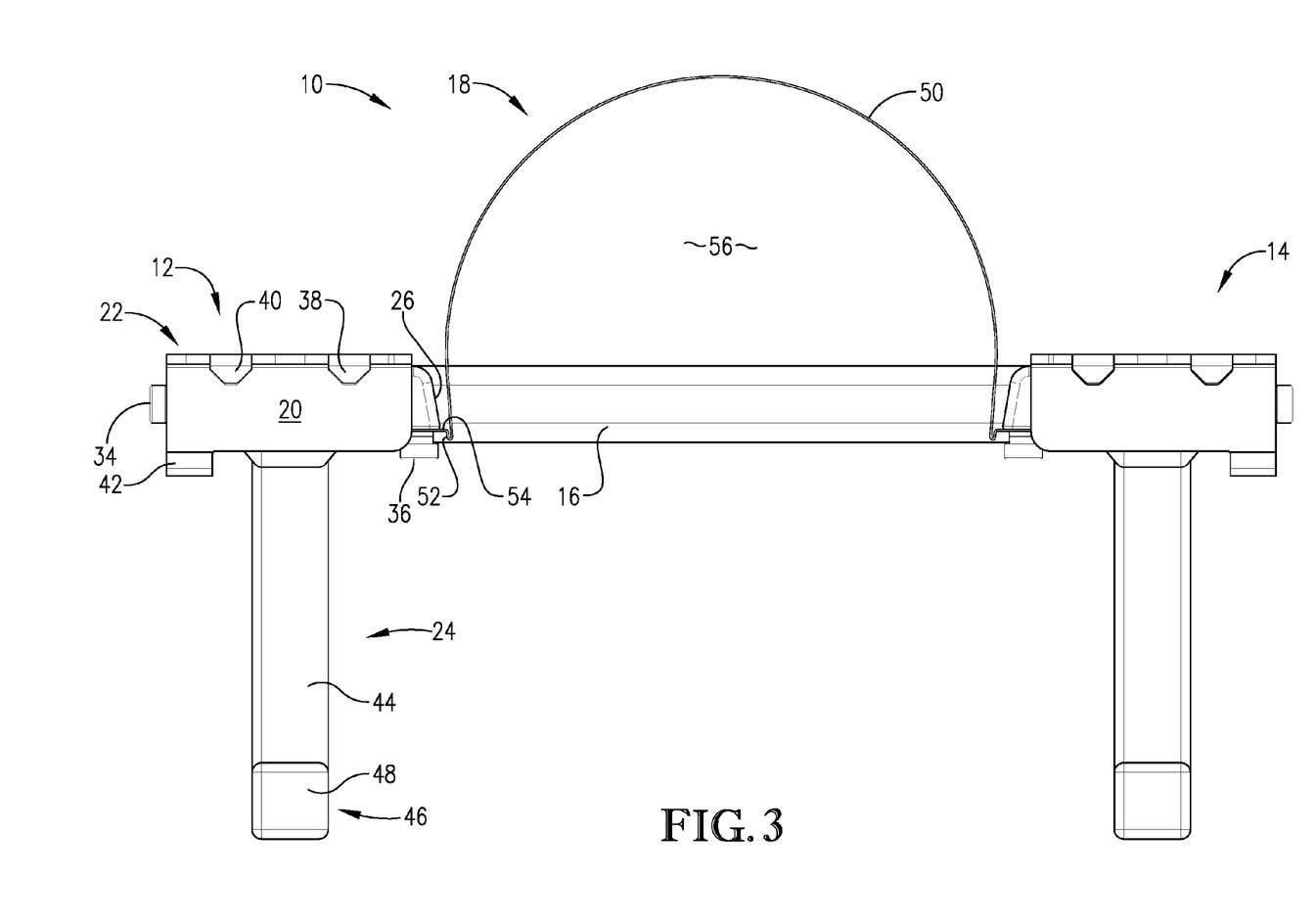
FIG. 3 is a front elevation view of the light shielding apparatus of FIG. 1.
Figure 4:
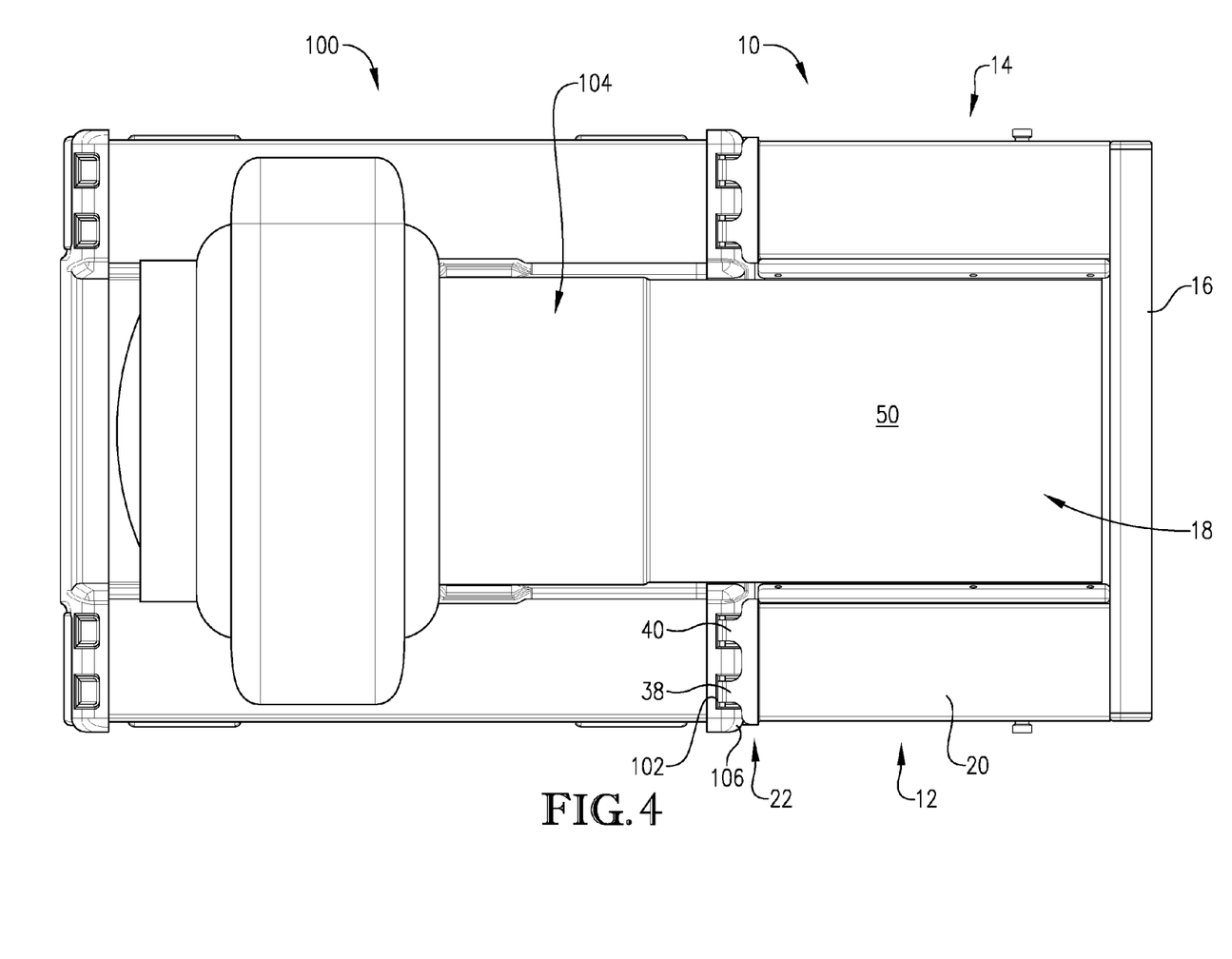
FIG. 4 is a plan view of the light shielding apparatus of FIG. 1.
Figure 5:
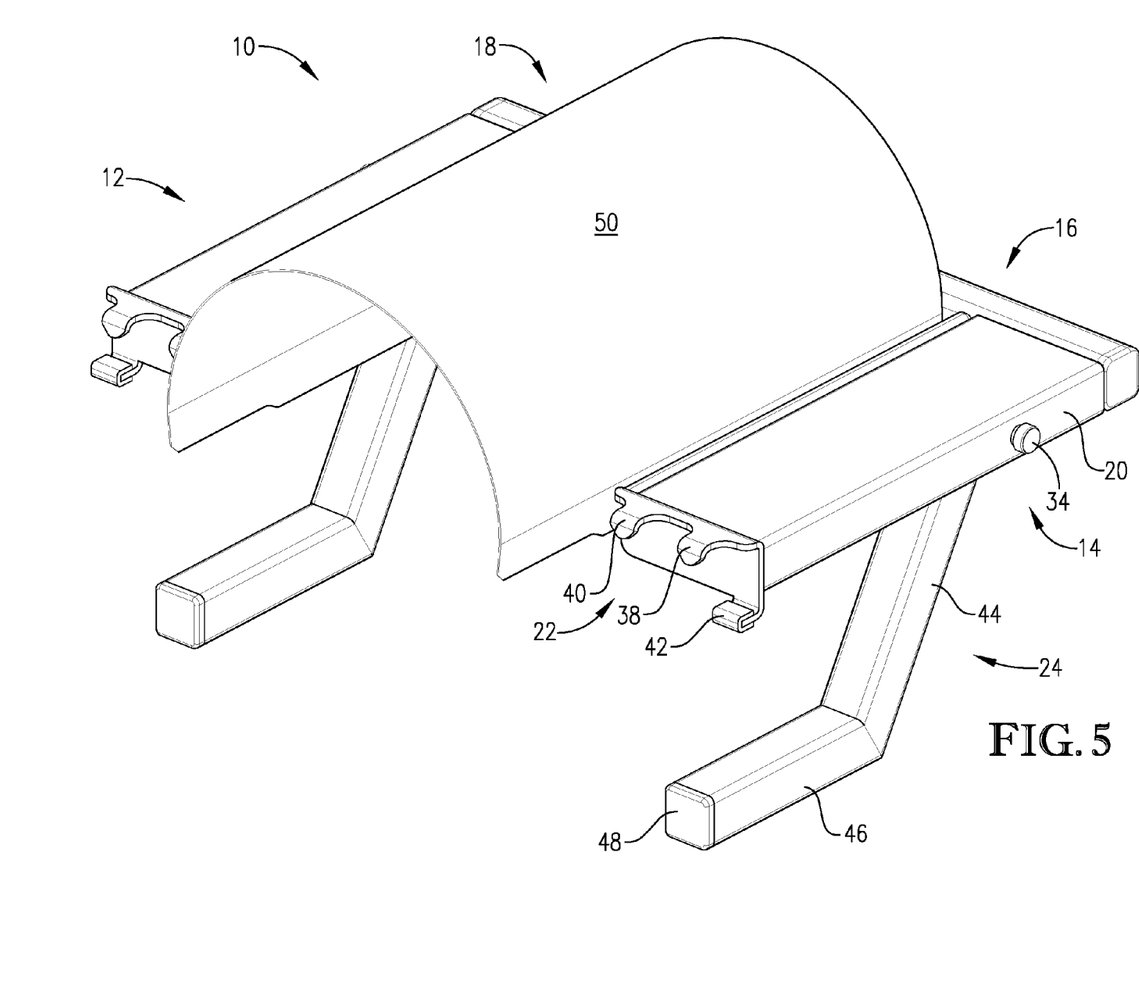
FIG. 5 is another perspective view of the light shielding apparatus of FIG. 1.

The mounting element 22 of each support assembly 12, 14 is provided for removably connecting the light shielding apparatus 10 to the electronic device 100 and broadly includes left and right hooks 38, 40 and a lower tab 42, as shown in FIGS. 3-5. The left and right hooks 38, 40 each may extend outwardly and downwardly from an upper portion of the proximal end of the primary support structure 20 and may be configured to engage slots 102 or other geometry of the electronic device 100. The lower tab 42 extends outwardly from a lower portion of the proximal end of the primary support structure 20 and ensures that the left and right hooks 38, 40 are not accidentally dislodged from or moved out of engagement with the slots 102 of the electronic device 100, as explained in more detail below. The mounting element 22 may be formed of machined rectangular tubing, fabricated metal, molded plastic, or any other suitable material.

Figure 1:
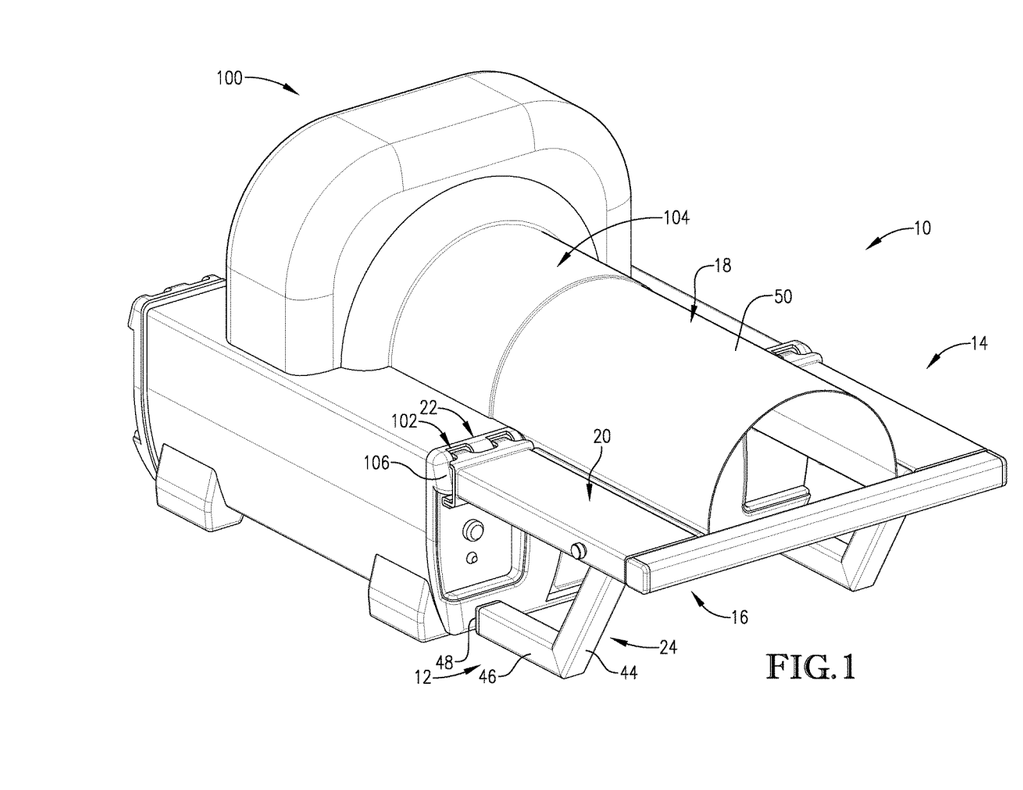
FIG. 1 is a perspective view of a light shielding apparatus constructed in accordance with an embodiment of the present invention and mounted on an X-ray device.
Figure 2:
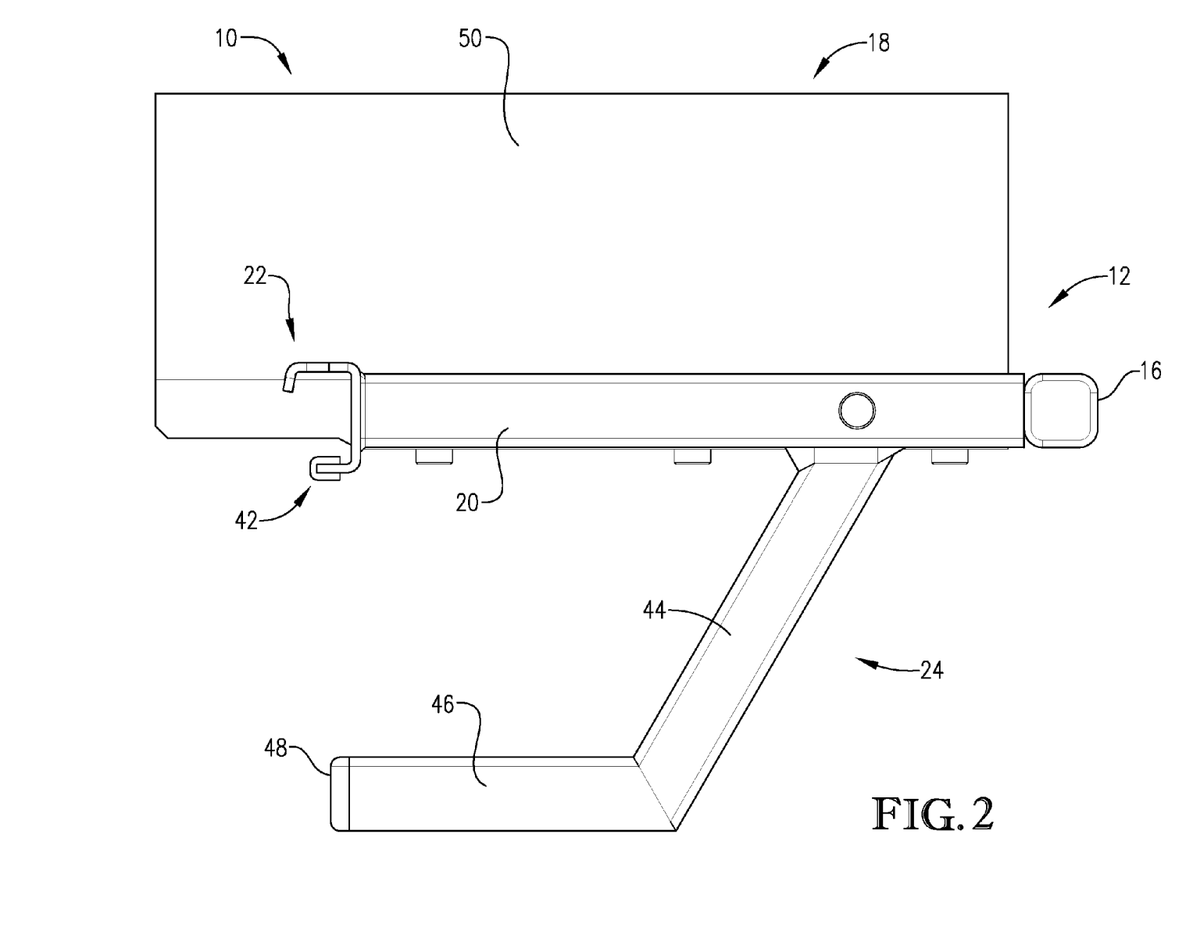
FIG. 2 is a side elevation view of the light shielding apparatus of FIG. 1.

The lower support member 24 retains the light shielding apparatus 10 in an upright orientation (i.e., in alignment with the electronic device) when the light shielding apparatus 10 is connected to the electronic device 100 and broadly includes a downwardly extending section 44 and a horizontally extending section 46, as best seen in FIG. 2. The downwardly extending section 44 provides vertical spacing between the horizontally extending section 46 and the primary support structure 20 and may be angled towards the proximal end of the primary support structure 20. The horizontally extending section 46 continues from the lower end of the downwardly extending section 44 horizontally towards the proximal end of the primary support structure 20. The horizontally extending section 46 terminates at an end 48 configured to contact a lower portion of the electronic device 100. The end 48 may include a flat, angled, or contoured (e.g., rounded) rubber pad or rubber stop for contacting the electronic device 100 without scratching it. The lower support member 24 may be formed of rectangular tubing, molded plastic, or any other suitable material. The lower support member 24 may be removably or shiftably connected to the primary support structure 20 via the support member fasteners 34. Alternatively, the lower support member 24 may be permanently attached to the primary support structure 20 via welding, adhesive, or interference fit.

The cross member 16 retains the left and right support assemblies 12, 14 in a coupled relationship with each other and may be connected to the primary support structures of the left and right support assemblies 12, 14 or the downwardly extending portions 44 of the lower support members 24 via fasteners inserted into the cross member fastener holes 30. The cross member 16 may be connected in one of a plurality of positions, as described in more detail below. The cross member 16 may be formed of rectangular tubing (FIGS. 1-5), bar stock (FIG. 6), molded plastic, or any other suitable material and may be any length, for dictating the spacing between the left and right support assemblies 12, 14.

The opaque shroud 18 blocks light from reaching the electronic device 100 and includes a cover 50, upturned or upwardly extending portions 52, and outwardly extending strips 54, as best seen in FIG. 3. The cover 50 may be extended between the primary support structures 20 of the left and right support assemblies 12, 14 and may take the shape of a cylindrical dome or similar shape when deployed so as to form a central space 56 covered from above. The cover 50 may have a radius larger than a radius of a scanner bed of the electronic device 100 and smaller than a radius of an end cap 104 of the electronic device 100. That is, the cover 50 may form an extension of the end cap 104 to provide additional protection. The cover 50 may be rigid or substantially flexible for being used with electronic devices of different sizes and shapes. The upturned portions 52 may extend upwards from the left and right edges of the cover 50 on outer sides of the cover 50 and may be fastened to the cover 50 via staples, stitches, adhesive, welding, or any other suitable means depending on the type of material forming the opaque shroud 18. The outwardly extending strips 54 extend away from the cover 50 from tops of the upturned portions 52 so as to form flaps or tabs on either side of the cover 50. The outwardly extending strips 54 may include fastener holes 58 for receiving the shroud fasteners 36 and may be elongated or open-ended slots for allowing the opaque shroud 18 to be adjusted relative to the support assemblies 12, 14, as described in more detail below. The opaque shroud 18 may be formed of canvas, rubber, plastic, sheet metal, or any other suitable material and may be substantially flexible for being folded and/or rolled up when not in use and for being adjustably positioned and shaped as desired when in use.

Use of the above-described light shielding apparatus 10 will now be described in more detail. First, the lower support members 24 may be connected to the primary support structures 20 of the left and right support assemblies 12, 14 via the support member fasteners 34. The opaque shroud 18 may then be connected to the left and right primary support structures 20 via the shroud fasteners 36. More specifically, the fastener holes 58 of the outwardly extending strips 54 of the opaque shroud 18 may be aligned with the shroud fastener holes 32 of the primary support structure 20 such that the shroud fasteners 36 may be inserted therethrough. The slotted shape of the fastener holes 58 may allow the opaque shroud 18 to be moved in relation to the primary support structure 20 before the shroud fasteners 36 are tightened. The cross member 16 may then be connected to the left and right support assemblies 12, 14 or the lower support members 24 via the cross member fastener holes 30 so as to couple the left and right support assemblies 12, 14 together. The cross member 16 may be connected in one of a plurality of positions such that the left and right support assemblies 12, 14 may be spaced apart from each other according to the size and shape of the electronic device. If the opaque shroud 18 is made of canvas or other non-rigid material, it may need to be unfolded or unrolled before attachment and manually urged into the cylindrical dome shape.

The light shielding apparatus 10 may be removably connected to the electronic device 100 as follows. First, the left and right hooks 38, 40 of the mounting elements 22 may be positioned near the slots 102 of the electronic device 100. The light shielding apparatus 10 may need to be pivoted upwards slightly such that the lower tabs 42 clear the mounting boss 106 of the electronic device 100 as the left and right hooks 38, 40 are lowered into the slots 102. The light shielding apparatus 10 may then be pivoted downwards until the lower support members 24 contact the lower portion of the electronic device 10 such that the light shielding apparatus 10 hangs from and rests against the front of the electronic device 10. The opaque shroud 18 should align with operative components of the electronic device 100 (e.g., optical lens of a camera) but may be adjusted as described above until light is substantially or completely blocked from reaching the operative components of the electronic device 100.

The light shielding apparatus 10 may then be removed from the electronic device 100 and disassembled as follows. First, the apparatus 10 may be pivoted upwards until the lower tabs 42 clear the mounting boss 106. The left and right hooks 38, 40 may then be slid upwards out of the slots 102 so as to be disconnected from the electronic device 100. The lower support members 24 and the cross member 16 may then be disconnected from the left and right support assemblies 12, 14 by removing the support member fasteners 34 and cross member fasteners. The opaque shroud 18 may also be disconnected from the primary support structures 20 and removed, folded, and/or rolled for storage.

The above-describe light shielding apparatus 10 provides many advantages over the prior art. For example, the light shielding apparatus 10 may be easily connected to the electronic device 100 without removing the electronic device 100 from its mount and may be used with many different sizes and types of electronic devices. For example, the left and right support assemblies 12, 14 may be spaced closer together or farther apart from each other for use on smaller or larger electronic devices such as X-ray devices having standard 14×17 phosphor panels and X-ray devices having larger 14×51 phosphor panels. The opaque shroud 18 may be flexed or adjusted to ensure that light is prevented from reaching the electronic device 100 between the front of the electronic device 100 and the opaque shroud 18 regardless of the shape of the front of the electronic device 100. The light shielding apparatus 10 may also protect the electronic device 100 from the elements and dust accumulation. In addition, the light shielding apparatus 10 is lightweight and can be disassembled for compact storage.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An apparatus for shielding an electronic device from light, the apparatus comprising:
   left and right support assemblies for supporting the apparatus on the electronic device, the left and right support assembly each including:
   primary support structure;
   a mounting element positioned near a proximal end of the primary support structure for removably connecting the support assembly to the electronic device; and
   a lower support member attached to the primary support structure and downwardly extending at an angle to abut a lower portion of the electronic device;
   an opaque shroud extending between the primary support structures of the left and right support assemblies, the opaque shroud being configured to block light from reaching the electronic device when the mounting elements are connected to the electronic device and the lower support members abut the lower portion of the electronic device.

2. The apparatus of claim 1, wherein the opaque shroud is configured to be urged into a downwardly curving shape.

3. The apparatus of claim 2, wherein the primary support structure of each support assembly includes a sloped surface for urging the opaque shroud into the downwardly curving shape.

4. The apparatus of claim 2, wherein the opaque shroud may be adjusted to have a radius larger than a radius of a scanner bed of the electronic device and smaller than a radius of an end cap of the electronic device.

5. The apparatus of claim 1, wherein the opaque shroud is formed of flexible material.

6. The apparatus of claim 5, wherein the opaque shroud is formed of a canvas material.

7. The apparatus of claim 1, further comprising a plurality of fasteners, the left and right primary support structures each including a fastener hole, the opaque shroud including left and right outwardly extending strips each having at least one fastener hole for receiving one of the fasteners therethrough and removably connecting the opaque shroud to the primary support structures.

8. The apparatus of claim 7, wherein the fastener holes of the left and right primary support structures and/or the fastener holes of the left and right outwardly extending strips are slotted such that the opaque shroud may be adjustably connected to the left and right primary support structures.

9. The apparatus of claim 7, wherein the fasteners are thumbscrews.

10. The apparatus of claim 7, wherein the opaque shroud includes a primary section having an outer side and left and right lower edges, and left and right upturned portions, the left and right outwardly extending strips extending from the left and right upturned portions.

11. The apparatus of claim 10, wherein the upturned portions are attached to the primary section via staples, stitching, glue, or other fastening means so as to reinforce the opaque shroud.

12. The apparatus of claim 1, wherein the mounting elements include one or more hooks for connecting the apparatus onto external mounting features of the electronic device.

13. The apparatus of claim 1, wherein the mounting elements include horizontally extending tabs spaced below the hooks and configured to engage the external mounting features of the electronic device such that the apparatus may be removed from the electronic device by pivoting the apparatus upwards until the horizontally extending tabs clear the external mounting features of the electronic device and then lifting the apparatus until the hooks clear the external mounting features of the electronic device.

14. The apparatus of claim 1, further comprising a cross member for rigidly connecting the left and right primary support structures together.

15. The apparatus of claim 1, wherein the opaque shroud extends past the primary support structures near a proximal end of the apparatus.

16. The apparatus of claim 1, wherein the left and right support assemblies are configured to be spaced closer or further apart from each other for being mounted on electronic devices of different sizes.

17. The apparatus of claim 1, wherein the primary support structures and the support members are formed of rectangular tubing.

18. An apparatus for shielding a phosphor panel of an X-ray device from light, the apparatus comprising:
   left and right support assemblies for supporting the apparatus on the X-ray device, the left and right support assembly each including:
      primary support structure;
      a mounting element positioned near a proximal end of the primary support structure for removably connecting the support assembly to the X-ray device; and
      a support member depending from the primary support structure and configured to abut a lower portion of the X-ray device;
   an opaque shroud extending between the primary support structures of the left and right support assemblies, the opaque shroud being configured to block light from reaching the phosphor panel when the apparatus is connected to the X-ray device and the support members abut the lower portion of the X-ray device.

19. The apparatus of claim 13, wherein the opaque shroud is configured to extend over 14" by 17" phosphor panels and 14" by 51" phosphor panels.

20. An apparatus for shielding a phosphor panel of an X-ray device from light, the apparatus comprising:
   left and right support assemblies for supporting the apparatus on the X-ray device, the left and right support assembly each including:
      primary support structure;
      a mounting element positioned near a proximal end of the primary support structure for removably connecting the support assembly to the X-ray device, the mounting element including:
         left and right hooks extending outwardly and downwardly from the proximal end of the primary support structure for being inserted into mounting slots of the X-ray device; and
         a lower tab extending outwardly from the proximal end of the primary support structure for preventing the left and right hooks from being inadvertently dislodged from the slots of the X-ray device; and
      a support member depending from the primary support structure and configured to abut a lower portion of the X-ray device, the support member including:
         a downwardly extending section angled towards the proximal end of the support member; and
         a horizontally extending section continuing from the downwardly extending section towards the proximal end of the primary support member; and
   an opaque shroud extending between the primary support structures of the left and right support assemblies, the opaque shroud including:
      a flexible canvas cover configured to take the shape of a cylindrical dome so as to form a central space covered from above;
      left and right upturned portions depending from the cylindrical dome on an outside of the cover; and
      left and right outwardly extending strips depending from the upturned portions and extending away from the cover, the outwardly extending strips having a plurality of slotted fastener holes for adjustably connecting the opaque shroud to the left and right primary support members, the opaque shroud being configured to block light from reaching the phosphor panel when the apparatus is connected to the X-ray device and the support members abut the lower portion of the X-ray device.

* * * * *